United States Patent [19]

Behre et al.

[11] Patent Number: 4,534,905
[45] Date of Patent: Aug. 13, 1985

[54] PROCESS FOR THE PREPARATION OF NITRONAPHTHALENE-SULPHONIC ACIDS

[75] Inventors: Horst Behre, Odenthal-Eikamp; Heinz U. Blank, Odenthal; Gerhard Burmeister, Leverkusen; Otto Lindner, Bergisch Gladbach, all of Fed. Rep. of Germany

[73] Assignee: Bayer Aktiengesellschaft, Leverkusen, Fed. Rep. of Germany

[21] Appl. No.: 265,271

[22] Filed: May 20, 1981

[30] Foreign Application Priority Data

May 29, 1980 [DE] Fed. Rep. of Germany ....... 3020441

[51] Int. Cl.$^3$ ........................................... C07C 143/24
[52] U.S. Cl. ................................................. 260/505 C
[58] Field of Search ................................... 260/505 C

[56] References Cited

FOREIGN PATENT DOCUMENTS 0013395  7/1980  European Pat. Off. ........ 260/505 C
2903849  8/1980  Fed. Rep. of Germany ... 260/505 C Primary Examiner—Alan Siegel
Attorney, Agent, or Firm—Sprung, Horn, Kramer & Woods

[57] ABSTRACT

Improved process for the preparation of nitronaphthalene-sulphonic acids by reacting the corresponding naphthalene-sulphonic acids with nitric acid and working up the nitration mixture, characterized by the features that the reaction of the naphthalene-sulphonic acids with nitric acid is already interrupted before the nitration reaction has ended and that the nitration mixture is treated, optionally after dilution with water, with bases at a pH value of 5 to 14.

9 Claims, No Drawings

PROCESS FOR THE PREPARATION OF NITRONAPHTHALENE-SULPHONIC ACIDS

The invention relates to a process for the preparation of nitronaphthalene-sulphonic acids by nitration of the corresponding naphthalene-sulphonic acids.

It is known that nitronaphthalene-sulphonic acids can be prepared by reacting the corresponding naphthalene-sulphonic acids, with nitric acid (see, for example, Ullmanns Enzyklopädie der technischen Chemie (Ullmann's Encyclopaedia of Industrial Chemistry), 3rd edition, volume 16, page 556, and 4th edition, volume 17, pages 108–115; N. Donaldson "The Chemistry and Technology of Naphthalene Compounds", London 1958, pages 158–163; N. N. Woroshzow "Grundlagen der Synthese von Zwischenprodukten und Farbstoffen" ("Basic Principles of the Synthesis of Intermediate Products and Dyestuffs"), Berlin 1966, pages 162–267; and Houben-Weyl Methoden der organischen Chemie (Methods of Organic Chemistry), 4th edition (1971), volume 10/1, page 636).

For example, the industrially important 8-nitronaphthalene-1,3,6-trisulphonic acid (nitro-T-acid) is prepared by nitrating the isomer mixture of naphthalenetrisulphonic acids which is obtained in the trisulphonation of naphthalene with sulphuric acid and oleum and contains, as the main constituent, naphthalene-1,3,6-trisulphonic acid, with nitric acid in sulphuric acid, as the solvent (see F.I.A.T., Final Report 1016, pages 32–39). In the preparation process known from the literature, a procedure is followed in which the hot solution of the naphthalenetrisulphonic acids in sulphuric acid, which solution has a temperature of 150° to 155° C. and is obtained in the trisulphonation of naphthalene, is cooled to 100° C., diluted with water and cooled further to 80° C. The batch is then transferred to the nitration kettle, cooled in this kettle to 35° to 40° C. and nitrated with mixed acid (86% of nitric acid, 12% of sulphuric acid and 2% of water) at 35° to 40° C. in the course of about 10 hours.

DE-OS (German Published Specification) 2,837,498 describes a process for the preparation of 8-nitronaphthalene-1,3,6-trisulphonic acid from naphthalene-1,3,6-trisulphonic acid or mixtures containing this compound by nitration with nitric acid in sulphuric acid, in which process nitration mixture which has reacted to the extent of at least 80% is initially introduced into the vessel, naphthalene-1,3,6-trisulphonic acid or a mixture containing this compound is added as a solution in sulphuric acid, 1 to 1.4 mols of nitric acid per mol of naphthalenesulphonic acid and, at the same time, if appropriate, water are added in a manner such that the sulphuric acid concentration during the nitration is 86 to 94% by weight, and the mixture is mixed thoroughly and the reaction temperature is kept at 30° to 60° C. The process can be carried out discontinuously or continuously, with a space/time yield of about 0.7 to 1.5 mols of nitro-T-acid per liter of container volume and hour, and, in the case of an optimum procedure, that is to say in the case of a discontinuous procedure, if the reaction mixture is allowed to after-react for a further 1 to 2 hours at 35° to 38° C. when the addition has ended, gives 8-nitronaphthalene-1,3,6-trisulphonic acid in a yield of 96%, relative to the naphthalene-1,3,6-trisulphonic acid employed.

The industrially important 8-nitronaphthalene-1,3,5-trisulphonic acid is prepared by nitrating the naphthalene-trisulphonic acid mixture which is obtained in the trisulphonation of naphthalene with sulphuric acid and oleum and which contains naphthalene-1,3,5-trisulphonic acid as the main constituent, with nitric acid using sulphuric acid as the solvent (see F.I.A.T. Final Report No. 1016, pages 42–44). According to this process, the hot solution, of the naphthalenetrisulphonic acids in sulphuric acid, which has a temperature of 90° C. and is obtained in the trisulphonation of naphthalene is transferred to the nitration kettle and, after cooling to 60° C., diluted with water and nitrated with mixed acid (86% of nitric acid, 12% of sulphuric acid and 2% of water) at 30° to 35° C. The nitration mixture is subsequently stirred at 40° C. for 1 hour. As a repetition of the process has shown, the yield of 8-nitronaphthalene-1,3,5-trisulphonic acid is only about 46%, relative to the naphthalene-1,3,5-trisulphonic acid employed (see Example 16 of the present Application).

The nitration of pure naphthalene-1,3,5-trisulphonic acid is described by H. E. Fierz-David et al., (Helv. Chim. Acta 35, (1952), pages 2139–2144). However, the nitration is associated with the formation of by-products, and therefore gives 8-nitronaphthalene-1,3,5-trisulphonic acid in a yield of only about 48%, even under very favourable conditions.

The nitration of 3-nitronaphthalene-1,5-disulphonic acid with nitric acid in sulphuric acid at 30° C. is described in German Patent Specification 72,665. The reaction time applied is 3 to 4 days. As repetition of this process has shown, the yield of 3,8-dinitronaphthalene-1,5-disulphonic acid is only 50%, relative to the 3-nitronaphthalene-1,5-disulphonic acid employed (see Example 19 of the present Application).

The common factor of all the known processes for the nitration of naphthalene-sulphonic acids is that they either give low yields and/or they require long nitration times. If the nitration is carried out continuously as described in DE-OS (German Published Specification) 2,837,498, relatively long after-reaction times are required in order to obtain the highest possible yield of the desired nitro compound. The end point of the nitration reaction is established by reducing a sample of the nitration mixture with zinc dust and determining the content of amino groups formed in the sample by diazotisation with sodium nitrite. The nitration reaction is ended as soon as the consumption of the diazotisation reagent no longer increases.

It has now been found that the abovementioned disadvantages of the known nitration processes, that is to say unsatisfactory yields and/or long reaction times and as a result poor space/time yields, can be eliminated by a procedure in which the nitration reaction is no longer brought to completion, as was hitherto the case, but is interrupted prematurely and the nitration mixture is treated with bases at a pH value of 5 to 14. A considerable increase in the space/time yields for all nitronaphthalene-sulphonic acids is achieved by the combination of these two measures. A considerable increase in yield is also achieved for nitronaphthalene-sulphonic acids which could hitherto be prepared only in unsatisfactory yields.

The invention thus relates to a process for the preparation of nitronapthalene-sulphonic acids by reacting the corresponding naphthalene-sulphonic acids with nitric acid and working up the nitration mixture thus obtained, which is characterised in that the reaction of the naphthalene-sulphonic acids with nitric acid is already interrupted before the nitration reaction has ended and the nitration mixture is treated, if appropriate after dilution with water, with bases at a pH value of 5 to 14, preferably 5 to 10.

The process according to the invention is particularly suitable for the preparation of nitronaphthalene-sulphonic acids of the formula (I)

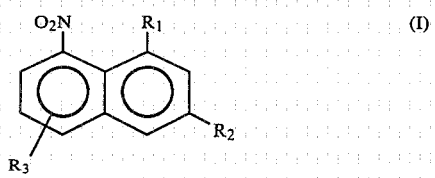

in which
R₃ is in the 5-position or 6-position,
R₁ and R₃ independently of one another represent a SO₃H group or NO₂ group and
R₂ represents a hydrogen atom or a SO₃H group or NO₂ group, with the proviso that at least one of the substituents R₁, R₂ or R₃ is a SO₃H group,
by nitrating (nitro)naphthalenesulphonic acids of the formula (II)

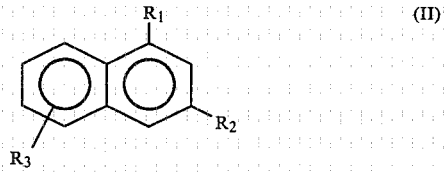

in which R₁, R₂ and R₃ have the meaning given under formula (I).

Examples which may be mentioned of naphthalene-sulphonic acids of the formula II which are particularly suitable for the process according to the invention are: naphthalene-1,3,6-trisulphonic acid, naphthalene-1,3,5-trisulphonic acid, naphthalene-1,5-disulphonic acid, 3-nitronaphthalene-1,5-disulphonic acid and 1,5-dinitronaphthalene-3-sulphonic acid.

Either the pure (nitro)naphthalene-sulphonic acids or mixtures containing these (nitro)naphthalene-sulphonic acids can be used in the process according to the invention.

Mixtures such as are obtained in the trisulphonation of naphthalene are preferably used for the nitration, according to the invention, of the naphthalene-1,3,6-trisulphonic acid. For example, it is possible to use the mixture which is obtained in the trisulphonation of naphthalene according to F.I.A.T. Final Report 1016, pages 29-39. The mixture prepared in this manner contains 40 to 48% by weight of naphthalenetrisulphonic acids in 100% strength sulphuric acid. The composition of this naphthalenesulphonic acid mixture is as follows: 75% by weight of naphthalene-1,3,6-trisulphonic acid, about 8% by weight of naphthalene-1,3,5-trisulphonic acid and about 12% by weight of naphthalene-1,3,7-trisulphonic acid. The sulphonation mixture can also additionally contain small amounts of other sulphonation products of naphthalene and/or oxidation products of naphthalene.

Naphthalene-1,3,6-trisulphonic acid mixtures which have been prepared another way can also be used in the process according to the invention.

Mixtures which contain naphthalene-1,3,5-trisulphonic acid and are dissolved in sulphuric acid, such as are obtained in the trisulphonation of naphthalene according to F.I.A.T. Final Report 1016, pages 42-44, are preferably used for the nitration, according to the invention, of the industrially important naphthalene-1,3,5-trisulphonic acid. These mixtures contain about 68% by weight of naphthalene-1,3,5-trisulphonic acid, 21% by weight of naphthalene-1,3,6-trisulphonic acid and 5% by weight of naphthalene-1,3,7-trisulphonic acid.

Naphthalene-1,3,5-trisulphonic acid mixtures which have been prepared another way can also be used in the process according to the invention.

Mixtures which contain 3-nitronaphthalene-1,5-disulphonic acid and are dissolved and/or suspended in sulphuric acid, such as are obtained, for example, in the nitration of naphthalene-1,5-disulphonic acid according to the process described in U.S. Pat. No. 2,191,820, can be used for the nitration of the industrially important 3-nitronaphthalene-1,5-disulphonic acid.

Mixtures which contain 3-nitronaphthalene-1,5-disulphonic acid and have been prepared another way can also be used in the process according to the invention.

It is an essential characteristic of the process according to the invention that the reaction of the naphthalene-sulphonic acids with nitric acid is already interrupted before the end of the nitration reaction. The progress of the nitration reaction in the nitration of naphthalenesulphonic acids is followed analytically. In the processes according to the state of the art, the nitration reaction has ended when the content of the desired nitronaphthalene-sulphonic acid in the nitration mixture no longer increases, that is to say when the highest possible yield (=yield which can be achieved in practice) of nitronaphthalene-sulphonic acid has been achieved.

According to the invention, however, the nitration reaction is already interrupted before this highest possible yield of the desired nitronaphthalene-sulphonic acid is reached. According to the invention, in particular, the nitration reaction is interrupted when more than 90% of the naphthalene-sulphonic acid employed has reacted, but the yield of the desired nitronaphthalene-sulphonic acid is only about 90% of the yield which can be achieved in practice. The yields which can be achieved in practice differ for the individual nitronaphthalene-sulphonic acids. Thus, for example, the yields of 8-nitronaphthalene-1,3,6-trisulphonic acid which can be achieved in practice are about 95% of the theoretical yield, whilst the yields of 8-nitronaphthalene-1,3,5-trisulphonic acid and 3,8-dinitronaphthalene-1,5-disulphonic acid which can be achieved in practice are only 50% of the theoretical yield.

The nitration reaction is therefore interrupted, for example in the case of the reaction of naphthalene-1,3,6-trisulphonic acid with nitric acid, as soon as more than 90% of the naphthalene-1,3,6-trisulphonic acid employed has reacted, and the yield of 8-nitronaphthalene-1,3,6-trisulphonic acid in the nitration mixture is at most 90%, relative to the naphthalene-1,3,6-trisulphonic acid employed. The nitration reaction is preferably interrupted as soon as more than 95%, in particular about 98%, of the naphthalene-1,3,6-trisulphonic acid employed has been consumed, and the yield of 8-nitronaphthalene-1,3,6-trisulphonic acid in the nitration mixture is at most 85%, preferably 70 to 80%, relative to the reacted naphthalene-1,3,6-trisulphonic acid.

In the reaction of naphthalene-1,3,5-trisulphonic acid with nitric acid, the nitration reaction is interrupted as soon as more than 90%, preferably more than 93% and in particular about 95 to 98%, of the naphthalene-1,3,5-trisulphonic acid employed has reacted, and the yield of 8-nitronaphthalene-1,3,5-trisulphonic acid in the nitration mixture is at most 50%, preferably at most 40%, in particular about 25 to 35%, relative to the reacted naphthalene-1,3,5-trisulphonic acid.

In the reaction of 3-nitro-naphthalene-1,5-disulphonic acid with nitric acid, the nitration reaction is interrupted as soon as more than 90%, preferably more than 93% and in particular about 95 to 98%, of the 3-nitronaphthalene-1,5-disulphonic acid employed has reacted, and the yield of 3,8-dinitronaphthalene-1,5-disulphonic acid is at most 50%, preferably at most 40% and in particular about 25 to 35%, relative to the reacted 3-nitronaphthalene-1,5-disulphonic acid.

The composition of the nitration mixtures when the nitration reaction is interrupted is determined as follows: the nitration mixture is first diluted, whilst cooling, by adding water or ice and the dilute acid solution is freed from nitrous gases, if appropriate by bubbling in air or nitrogen, and then analysed by high pressure liquid chromatography, using an acid eluting agent.

In the case of the preparation of naphthalene-trisulphonic acids and/or nitronaphthalene-disulphonic acids, the napthalene-sulphonic acids to be nitrated are reacted with nitric acid, until the nitration reaction is interrupted, in 85 to 95% strength by weight, preferably 88 to 92% strength by weight, sulphuric acid at temperatures from 0° to 50° C., preferably 10° to 40° C. 1.05 to 2.5 mols, preferably 1.15 to 2.0 mols, of nitric acid are used per mol of (nitro)naphthalene-di(mono)sulphonic acid to be nitrated.

In the case of the preparation of naphthalene-disulphonic acids, the reaction with nitric acid is carried out in 70 to 90% strength by weight, preferably 75 to 85% strength by weight, sulphuric acid.

The reaction of the naphthalenesulphonic acids with nitric acid can also be carried out in excess 80 to 100% strength by weight, preferably 90 to 98% strength by weight, nitric acid at temperatures from $-40°$ to $+20°$.

The reaction times for the reaction of naphthalenesulphonic acids with nitric acid up to interruption of the nitration reaction depend on the temperature and/or the sulphuric acid concentration or nitric acid concentration (if nitric acid is used as the solvent) and/or the excess of nitric acid and/or the initial concentration of the naphthalene-sulphonic acids in the reaction mixture, and in general are about a few minutes to several hours. For example, the reaction time for the reaction of one mol of naphthalene-1,3,6-trisulphonic acid with 1.15 mols of 98% strength by weight nitric acid in 4.5 mols of 90% strength by weight sulphuric acid at 30° C., up to interruption of the nitration reaction, is about 20 minutes. In the case of the reaction of one mol of naphthalene-1,3,5-trisulphonic acid in 23 mols of 98% strength by weight nitric acid at $-20°$ C., the reaction time up to interruption of the nitration reaction is about 130 minutes, whilst in the case of the reaction of one mol of 3-nitronaphthalene-1,5-disulphonic acid with 2 mols of nitric acid in 15 mols of 90% strength by weight sulphuric acid at 10° C., a reaction time, up to interruption of the nitration reaction, of about 3 hours is required.

When the process according to the invention is carried out industrially, in particular in the case of a discontinuous procedure, it may be difficult to maintain the short reaction times up to interruption of the nitration reaction, because of the large amount of heat of reaction to be removed. In this case, it may be advantageous to carry out the reaction of the naphthalene-sulphonic acids with nitric acid in the presence of alkali metal sulphates, but preferably ammonium sulphate. The alkali metal sulphates act as reaction retarders. If the reaction is carried out in sulphuric acid as the solvent, the alkali metal sulphates can be added before and/or during the addition of the nitric acid. However, it is also possible to produce the alkali metal sulphates in situ in the reaction mixture, for example by using the naphthalene-sulphonic acids in the form of their alkali metal salts and/or adding the nitric acid in the form of alkali metal nitrates.

The alkali metal sulphates are used in amounts of 0.1 to 1 mol, preferably 0.25 to 0.75 mol, per sulpho group of the naphthalene-sulphonic acid to be reacted.

The interruption, according to the invention, of the nitration reaction can be effected in a manner which is in itself known, for example by lowering the nitric acid concentration to a concentration which is no longer sufficient for the nitration, and/or by cooling. The nitric acid concentration can be lowered in various ways. It is usually lowered by diluting the nitration mixture with water. Cooling ensures that the temperature does not exceed 100° C. during dilution. However, the nitric acid concentration can also be lowered by distilling off nitric acid. The reaction mixture obtained in this manner is then subjected to the treatment, according to the invention, with bases at a pH value of 5 to 14.

However, it is also possible to interrupt the nitration reaction by a procedure in which the bases with which it is intended to carry out the base treatment according to the invention are added directly to the nitration mixture. That is to say, premature interruption, according to the invention, of the nitration reaction and the treatment, according to the invention, of the nitration mixture with bases are carried out in a single process step.

Examples which may be mentioned of bases which can be used in the process according to the invention are: inorganic bases, such as alkali metal hydroxides, oxides, carbonates or bicarbonates, alkaline earth metal hydroxides, oxides, carbonates or bicarbonates and ammonia, and organic bases, such as aliphatic, araliphatic, aromatic and heterocyclic amines. Examples of aliphatic amines which may be mentioned are: methylamine, triethylamine, tributylamine and cyclohexylamine; examples of araliphatic amines which may be mentioned are dimethylbenzylamine; examples of aromatic amines which may be mentioned are dimethylaniline and diethylaniline; and examples of heterocyclic amines which may be mentioned are pyridine, piperidine and morpholine.

For economic reasons, the inorganic bases, especially ammonia, are preferably used.

The treatment, according to the invention, of the nitration mixtures with bases is carried out at temperatures from $-10°$ to $+130°$ C., preferably 10° to 80° C. The pH value of the aqueous nitration mixtures to which the bases have been added is 5 to 14, preferably 5 to 10.

The period of treatment is established by analytical investigation of the reaction solutions. The treatment is ended as soon as the content of the desired nitro-naphthalenesulphonic acid in the reaction solutions does not increase further.

Instead of a single base, it is also possible to use various bases, and to add these various bases in stages. For example, it is possible, in a first stage, initially to bring the strongly acid nitration mixture to a pH value of 4 to 5 with cheap inorganic bases, for example calcium carbonate, and then to adjust the still acid mixture to the desired pH value of between 5 and 14, preferably 5 and 10, with ammonia and/or an organic base, if appropriate after removing sparingly soluble inorganic salts (for example gypsum) which have been formed.

In the nitration of naphthalene-1,3,6-trisulphonic acid, it has proved suitable to react the nitration mixture, which has been diluted, if appropriate, with water, with the abovementioned inorganic and/or organic bases at a pH value of 5 to 10 and at temperatures of $-10°$ to $+130°$ C., until the content of 8-nitronaphthalene-1,3,6-trisulphonic acid in the nitration mixture no longer rises.

In the nitration of naphthalene-1,3,5-trisulphonic acid or 3-nitronaphthalene-1,5-disulphonic acid, it has proved appropriate to treat the nitration mixture, which has been diluted with water, if appropriate, with ammonia and/or the abovementioned organic bases at a pH value of 5 to 10 and at temperatures of $-10°$ to $+80°$ C., until the content of 8-nitronaphthalene-1,3,5-trisulphonic acid or 3,8-dinitronaphthalene-1,5-disulphonic acid in the nitration mixture no longer increases.

In addition to the abovementioned advantages of the process according to the invention, that is to say substantially increased space/time yields and/or yields, the process according to the invention furthermore has the advantage that the amount of nitrous gases thereby obtained is considerably less than the amount obtained in the known processes.

The process according to the invention can be carried out either discontinuously or continuously.

The nitronaphthalene-sulphonic acids prepared according to the invention are important intermediate products for the preparation of dyestuffs.

Unless otherwise indicated, the percentage data used in the following examples relate to the percentage by weight.

EXAMPLE 1

400 g of a naphthalene-trisulphonic acid mixture, which has been obtained as described below, are initially introduced into a 1 l four-necked flask provided with 2 metering dropping funnels, a thermometer and a sabre-shaped stirrer. 40 g of water and 100 g of 90% strength sulphuric acid are first added dropwise to the sulphonation mixture at 30° C., whilst cooling. 38 g (0.59 mol) of 98% strength nitric acid are then added dropwise in the course of 5 minutes, whilst cooling and stirring. The reaction mixture is subsequently stirred at 30° C. for 10 minutes. It is then poured, at 5° to 10° C., onto 500 g of ice in the course of 5 minutes. The solution formed is freed from the nitrous gases by passing in air. The dilute reaction solution thus obtained is diluted with water to 1 l.

The composition of the solution is determined by means of high pressure liquid chromatography, using an acid eluting agent. The values found are given below.

|  | Content [g/l] | Yield, relative to the particular trisulphonic acid [mol %] |
| --- | --- | --- |
| 1-Nitronaphthalene-3,6,8-trisulphonic acid | 23.6 | 47 |
| 1-Nitronaphthalene-4,6,8-trisulphonic acid | 53.5 | 33.5 |
| Naphthalene-1,3,5-trisulphonic acid | 3.4 | 2.5 |
| Naphthalene-1,3,6-trisulphonic acid | 0.45 | 1.5 |

1 l of the dilute nitration solution described above and about 720 ml of 25% strength aqueous ammonia solution are simultaneously allowed to run, whilst cooling at 0° to 5° C. and at a pH value of 9, into a 3 l five-necked flask provided with 2 metering dropping funnels, an internal thermometer, a pH electrode and a stirrer. The reaction solution is subsequently stirred at 20° C. for 2 hours, its pH value being kept at 9, if appropriate by adding further ammonia solution. The solution is then diluted with water to 2 l. High pressure liquid chromatography of the solution thus obtained gives the following content of (nitro)naphthalene-trisulphonic acids:

|  | Content [g/l] | Yield, the relative to the particular trisulphonic acid [mol %] |
| --- | --- | --- |
| 1-Nitro-naphthalene-3,6,8-trisulphonic acid | 14.8 | 96.5 |
| 1-Nitro-naphthalene-4,6,8-trisulphonic acid | 62.7 | 78.5 |
| Naphthalene-1,3,5-trisulphonic acid | 2.4 | 3.5 |
| Naphthalene-1,3,6-trisulphonic acid | 0.3 | 2.0 |

The trisulphonation mixture used as the starting material had been obtained as follows.

385 g of 100% strength sulphuric acid were initially introduced into a 2 l four-necked flask provided with a metering screw, a metering dropping funnel, an internal thermometer and a sabre-shaped stirrer. 380 g of a disulphonation mixture were introduced via the metering screw in the course of 30 minutes, whilst stirring. The disulphonation mixture had the following composition: 58% of naphthalene-1,5-disulphonic acid, 7.6% of naphthalene-1,6-disulphonic acid, 3.0% of naphthalene-1,7-disulphonic acid, 2.2% of naphthalene-1,3,5-trisulphonic acid, 4.5% of naphthalene-1,3,6-trisulphonic acid, 0.4% of naphthalene-1,3,7-trisulphonic acid and 24.3% of $SO_3$, and had been obtained as follows.

Solutions of 128 g (1 mol) of naphthalene in 640 g of methylene chloride and 243 g of $SO_3$ in 950 g of methylene chloride were simultaneously metered into initially introduced methylene chloride at a rate such that the temperature could be kept between $-5°$ and $-10°$ C. When the addition had ended, the reaction mixture was kept at $-5°$ to $-10°$ C. for 1.5 hours and then evaporated to dryness in vacuo.

Whilst metering in the disulphonation mixture described above, the reaction mixture was warmed to 70° C. 42 g of oleum (65% strength) were then added dropwise via the metering dropping funnel. The reaction mixture was stirred at 90° C. for 7 hours.

The composition of the trisulphonation mixture (naphthalene-trisulphonic acid mixture) thus obtained was: 35.5% of naphthalene-1,3,5-trisulphonic acid, 6.8% of naphthalene-1,3,6-trisulphonic acid, 1.3% of naphthalene-1,3,7-trisulphonic acid and 56% of sulphuric acid. The carbon content of the sulphonation mixture was 14.7%.

EXAMPLE 2

11 ml of a solution of nitric acid in 90% strength sulphuric acid (content of nitric acid in the solution: 63 g/l = 1.0 mol/l) are added to 40 ml of a solution of naphthalene-1,3,6-trisulphonic acid in 90% strength sulphuric acid (content of naphthalene-1,3,6-trisulphonic acid: 92 g/l = 0.25 mol/l) at 20° C. in the course of 10 minutes, whilst cooling. The reaction solution is subsequently stirred at 20° C. for 15 minutes, poured onto 65 g of ice and made up to 200 ml with water in a measuring flask. The content of nitro-naphthalene-trisulphonic acids in the reaction solution thus obtained is determined by high pressure liquid chromatography, using an acid eluting agent. The content is:

|  | Content [g/l] | Yield, relative to naphthalene-1,3,6-trisulphonic acid [mol %] |
|---|---|---|
| Naphthalene-1,3,6-trisulphonic acid | 0.24 | 1.3 |
| 1-Nitronaphthalene-3,6,8-trisulphonic acid | 14.2 | 69 |
| 2-Nitronaphthalene-3,6,8-trisulphonic acid | 0.14 | 0.5 |
| 1-Nitronaphthalene-2,5,7-trisulphonic acid | 0.68 | 3.3 |

50 ml of the dilute nitration solution described above are adjusted to a pH value of 9 at 0° C. by adding 25% strength aqueous ammonia solution, and the solution is kept at this pH value for 2 hours. It is then made up to 200 ml with water in a measuring flask. Investigation of the resulting solution by high pressure liquid chromatography gives the following content of (nitro)naphthalene-trisulphonic acids:

|  | Content [g/l] | Yield, relative to naphthalene-1,3,6-trisulphonic acid [mol %] |
|---|---|---|
| Naphthalene-1,3,6-trisulphonic acid | 0.06 | 1.3 |
| 1-Nitronaphthalene-3,6,8-trisulphonic acid | 4.95 | 96 |
| 2-Nitronaphthalene-3,6,8-trisulphonic acid | 0.04 | 0.5 |
| 1-Nitronaphthalene-2,5,7-trisulphonic acid | 0.17 | 3.3 |

EXAMPLE 3

25 ml of a solution of nitric acid in 90% strength sulphuric acid (content of nitric acid: 63 g/l = 1.0 mol/l) are added to 200 ml of a solution of naphthalene-1,3,6-trisulphonic acid in 90% strength sulphuric acid (content of naphthalene-1,3,6-trisulphonic acid in the solution: 37.5 g/l = 0.102 mol/l) at 0° C. in the course of 15 minutes, whilst cooling. The reaction solution is subsequently stirred at 0° C. for 90 minutes and then poured onto 200 g of ice and made up to 500 ml with water in a measuring flask.

In each case 50 ml of the dilute nitration mixture solution thus obtained are adjusted to different pH values at 0° C. using different bases, and after the mixtures have been kept at these pH values for 2 hours, they are made up to 500 ml with water.

The composition of the reaction solutions thus obtained is determined by means of high pressure liquid chromatography, using an acid eluting agent.

In order to demonstrate the effect of the base treatment, 50 ml of the untreated dilute nitration solution are made up to 500 ml with water and the content of the solution is determined by high pressure liquid chromatography, using an acid eluting agent (Example 3a).

The experimental conditions and the results of the experiments are summarised in Table 1 which follows.

TABLE 1

| Example | Base | pH value | Content [g/l] 1,3,6-SO₃H | Content [g/l] 1-NO₂—3,6,8-SO₃H | Content [g/l] 2-NO₂—3,6,8-SO₃H | Content [g/l] 1-NO₂—2,5,7-SO₃H | Yield [mol %] 1,3,6-SO₃H | Yield [mol %] 1-NO₂—3,6,8-SO₃H | Yield [mol %] 2-NO₂—3,6,8-SO₃H | Yield [mol %] 1-NO₂—2,5,7-SO₃H |
|---|---|---|---|---|---|---|---|---|---|---|
| 3a | — | <1 | 0.046 | 1.102 | 0.008 | 0.034 | 3.0 | 65 | 0.4 | 2.0 |
| b | NH₃ | 6 | 0.039 | 1.641 | 0.007 | 0.037 | 2.6 | 97 | 0.5 | 2.2 |
| c | NH₃ | 8 | 0.041 | 1.638 | 0.009 | 0.036 | 2.7 | 97 | 0.5 | 2.1 |
| d | NH₃ | 10 | 0.038 | 1.586 | 0.007 | 0.030 | 2.5 | 94 | 0.5 | 1.8 |
| e | NaOH | 10 | 0.040 | 1.596 | 0.008 | 0.033 | 2.6 | 94 | 0.5 | 1.9 |
| f | KOH | 10 | 0.044 | 1.645 | 0.009 | 0.037 | 2.9 | 97 | 0.5 | 2.2 |

EXAMPLE 4

120 ml of a solution of nitric acid in 90% strength sulphuric acid (content of nitric acid: 63 g/l = 1.0 mol/l) are added to 500 ml of an equimolar solution of naphthalene-1,3,5-trisulphonic acid and naphthalene-1,3,6-trisulphonic acid in 90% strength sulphuric acid (content of the solution: in each case 36.8 g/l = 0.1 mol/l of 1,3,5- and 1,3,6-trisulphonic acid) at 20° C. in the course of 15 minutes, whilst cooling. The reaction solution is subsequently stirred at 20° C. for 45 minutes, poured onto 500 g of ice and made up to 2 l with water in a measuring flask.

50 ml portions of the dilute nitration solution thus obtained are adjusted to various pH values in the range from 7 to 10 at various temperatures using aqueous ammonia.

The composition of the reaction solutions thus obtained is then determined by means of high pressure liquid chromatography, using an acid eluting agent. The experimental conditions and the yields of nitronaphthalene-trisulphonic acids are summarised in Table 2 which follows (Example 4a is a comparison experiment without the addition of a base).

TABLE 2

| Example | Temperature °C. | pH value | Base | Yield [mol %] 1-NO₂—3,6,8-SO₃H | Yield [mol %] 1-NO₂—4,6,8-SO₃H |
|---|---|---|---|---|---|
| 4a | 20 | <1 | — | 77 | 35 |
| b | 0 | 7 | NH₃ | 96.5 | 79 |
| c | 0 | 8 | NH₃ | 97 | 82.5 |
| d | 0 | 9 | NH₃ | 98 | 83 |

TABLE 2-continued

| Example | Temperature °C. | pH value | Base | Yield [mol %] 1-NO$_2$—3,6,8-SO$_3$H | 1-NO$_2$—4,6,8-SO$_3$H |
|---|---|---|---|---|---|
| e | 0 | 10 | NH$_3$ | 96.5 | 82.5 |
| f | 20 | 7 | NH$_3$ | 96.5 | 80 |
| g | 40 | 7 | NH$_3$ | 95 | 82.5 |
| h | 60 | 7 | NH$_3$ | 94 | 77.5 |
| i | 20 | 9 | NH$_3$ | 95 | 80.5 |
| k | 40 | 9 | NH$_3$ | 95 | 80.5 |
| l | 60 | 9 | NH$_3$ | 96 | 81 |

EXAMPLE 5

60 ml of a solution of nitric acid in 90% strength sulphuric acid (content of nitric acid: 75.6 g/l=1.2 mols/l) are added to 200 ml of a solution of naphthalene-1,3,5-trisulphonic acid in 90% strength sulphuric acid (content of naphthalene-1,3,5-trisulphonic acid in the solution: 92 g/l=0.25 mol/l) at 20° C. in the course of 15 minutes, whilst cooling. The reaction mixture is subsequently stirred at 20° C. for 20 minutes, poured onto 200 g of ice and diluted with water to 500 ml in a measuring flask.

50 ml portions of the dilute reaction solution are adjusted to a pH value of 9 at 0° C. using various bases. The composition of the reaction solutions is then determined by means of high pressure liquid chromatography, using an acid eluting agent. The bases used and the yields obtained with them are summarised in Table 3 which follows. Example 5a is a comparison experiment without the addition of a base.

TABLE 3

| Example | Base | 1,3,5-SO$_3$H | Yield [mol %] 1-NO$_2$— 4,6,8-SO$_3$H | 2-NO$_2$— 4,6,8-SO$_3$H |
|---|---|---|---|---|
| 5a | — | 2.0 | 28 | 4.1 |
| b | Ammonia | 2.3 | 75 | 4.2 |
| c | Methylamine | 4.0 | 72 | 5.9 |
| d | Ethylamine | 4.0 | 72 | 6.0 |
| e | Ethylenediamine | 2.9 | 70 | 4.0 |
| f | Dimethylamino-pyridine | 2.5 | 70 | 5.8 |
| g | Ammonia + 5 ml of pyridine | 1.8 | 85 | 5.9 |

EXAMPLE 6

11 ml of a solution of nitric acid in 90% strength sulphuric acid (content of nitric acid: 31.5 g/l=0.5 mol/l) are added to 50 ml of a solution of 3-nitronaphthalene-1,5-disulphonic acid (nitro-Armstrong acid) in 90% strength sulphuric acid (content of nitro-Armstrong acid: 16.65 g/l=0.05 mol/l) at 20° C. in the course of 15 minutes, whilst cooling. The reaction mixture is stirred at 20° C. for 1 hour and then poured onto 100 g of ice and made up to 250 ml with water.

50 ml of the dilute acid nitration solution are adjusted to a pH value of 9 at 0° C. using 25% strength aqueous ammonia solution, and the solution is kept at this pH value at 20° C. for 2 hours.

The composition of the reaction solutions thus obtained is determined by means of high pressure liquid chromatography, using an acid eluting agent.

The yields of nitronaphthalene-sulphonic acids in the acid reaction solution and in the reaction solution which has been treated with ammonia are compared with one another below.

| Reaction products | Yield [mol %] Acid reaction solution | Reaction solution which has been treated with ammonia |
|---|---|---|
| 3,8-Dinitronaphthalene-1,5-disulphonic acid | 30 | 89 |
| 3,7-Dinitronaphthalene-1,5-disulphonic acid | 5.4 | 5.8 |
| 3-Nitronaphthalene-1,5-disulphonic acid | 5.5 | 5.8 |

EXAMPLE 7

The nitration of 3-nitro-naphthalene-1,5-disulphonic acid is carried out as described in Example 6, but the nitric acid excess, the reaction temperature and the after-reaction time are changed in the individual experiments. The conditions applied in the individual experiments and the results obtained under these conditions are summarised in the following table.

TABLE 4

| Example | HNO$_3$ excess (%) | Reaction temperature (°C.) | After-reaction time (h) | Base | Yield [mol %] 3,8-NO$_2$—1,5-SO$_3$H | 3,7-NO$_2$—1,5-SO$_3$H | 3-NO$_2$—1,5-SO$_3$H |
|---|---|---|---|---|---|---|---|
| 7a | 150 | 20 | 1 | none | 29,5 | 5,9 | 4,3 |
|    |     |    |   | ammonia | 87 | 5,7 | 4,3 |
| b | 200 | 20 | 1 | none | 30 | 5,7 | 2,5 |
|    |     |    |   | ammonia | 85 | 5,4 | 2,5 |
| c | 100 | 20 | 2 | none | 29 | 6,4 | 3,3 |
|    |     |    |   | ammonia | 89 | 6,0 | 3,3 |
| d | 100 | 40 | 1 | none | 46,5 | 5,7 | 4,2 |
|    |     |    |   | ammonia | 77 | 5,5 | 5,4 |

EXAMPLE 8

A suspension of 184 g (0.5 mol) of naphthalene-1,3,6-trisulphonic acid in 90% strength sulphuric acid is initially introduced into a 1 l three-necked flask provided with a metering dropping funnel, an internal thermometer and a sabre-shaped stirrer. 37 g (0.575 mol) of 98% strength nitric acid are added dropwise to the suspension at 30° C. in the course of 10 minutes, whilst stirring. The reaction mixture is subsequently stirred at 30° C. for 10 minutes and is then introduced, at a temperature which does not exceed 40° C., into 425 g of ice-water. After driving off the nitrous gases by passing in air, the reaction solution is made up to 1 l with water. The composition of the nitration solution thus obtained is determined by means of high pressure liquid chromatography, using an acid eluting agent. The solution has the following content of (nitro)naphthalene-sulphonic acids:

|  | Content (g/l) | Yield, relative to naphthalene-1,3,6-trisulphonic acid (mol %) |
|---|---|---|
| 1-Nitronaphthalene-3,6,8-trisulphonic acid | 161.0 | 78 |
| 2-Nitronaphthalene-3,6,8-trisulphonic acid | 1.0 | 0.5 |
| 1-Nitronaphthalene-2,5,7-trisulphonic acid | 8.3 | 4.0 |
| Naphthalene-1,3,6-trisulphonic acid | 0.7 | 0.4 |

1000 ml of the acid dilute nitration mixture solution described above and an approximately 50% strength aqueous calcium carbonate suspension are simultaneously allowed to run into a solution of 106.5 g (0.75 mol) of sodium sulphate in 500 ml of water at 60° to 70° C., whilst maintaining a pH value of 3 to 4. The mixture thus obtained is subsequently stirred at 60° to 70° C. for 30 minutes. The gypsum which has precipitated is then filtered off and washed with warm water until the runnings are colourless.

The filtrate and runnings are combined and are adjusted to a pH value of 9 by adding about 10 ml of saturated aqueous sodium carbonate solution at 20° C. The calcium carbonate which has precipitated is filtered off and washed with warm water. The filtrate and runnings are combined and made up to 2 l with water. The composition of the solution thus prepared is determined by means of high pressure liquid chromatography, using an acid eluting agent. The solution has the following content of nitro-naphthalene-sulphonic acids:

|  | Content (g/l) | Yield, relative to naphthalene-1,3,6-trisulphonic acid (mol %) |
|---|---|---|
| 1-Nitronaphthalene-3,6,8-trisulphonic acid | 104.3 | 96 |
| 2-Nitronaphthalene-3,6,8-trisulphonic acid | 0.6 | 0.5 |
| 1-Nitronaphthalene-2,5,7-trisulphonic acid | 4.0 | 3.7 |
| Naphthalene-1,3,6-trisulphonic acid | 0.27 | 0.3 |

EXAMPLE 9

397 g of a trisulphonation mixture which had been obtained according to the process described in DE-OS (German Published Specification) 2,718,207 are initially introduced into the nitration apparatus described in Example 1. This mixture had the following composition: 3.7% of naphthalene-1,3,5-trisulphonic acid, 36.2% of naphthalene-1,3,6-trisulphonic acid, 5.6% of naphthalene-1,3,7-trisulphonic acid and 55% of sulphuric acid.

The carbon content of the sulphonation mixture was 15.1%.

35 g of water and 50 g of 90% strength sulphuric acid are first added dropwise to this trisulphonation mixture at 30° C., whilst cooling. 39 g (0.6 mol) of 98% strength nitric acid are then added dropwise in the course of 10 minutes, whilst cooling and stirring. The reaction mixture is subsequently stirred at 30° C. for 10 minutes. It is then introduced into 450 g of ice-water, during which a temperature of 30° C. is not exceeded. The nitrous gases are driven off from the resulting solution by passing in air. The dilute reaction solution is made up to 1 l with water.

The composition of the dilute nitration mixture solution thus obtained is determined by means of high pressure liquid chromatography, using an acid eluting agent. The solution has the following content of nitronaphthalene-sulphonic acids:

|  | Content (g/l) | Yield, relative to the particular naphthalenetrisulphonic acid (mol %) |
|---|---|---|
| 1-Nitronaphthalene-3,6,8-trisulphonic acid | 129.2 | 80.0 |
| 2-Nitronaphthalene-3,6,8-trisulphonic acid | 0.32 | 0.2 |
| 1-Nitronaphthalene-2,5,7-trisulphonic acid | 5.5 | 3.4 |
| Naphthalene-1,3,6-trisulphonic acid | 0.43 | 0.3 |
| 1-Nitronaphthalene-4,6,8-trisulphonic acid | 6.0 | 36.5 |
| 2-Nitronaphthalene-4,6,8-trisulphonic acid | 0.91 | 5.5 |
| Naphthalene-1,3,5-trisulphonic acid | 0.37 | 2.5 |
| 1-Nitronaphthalene-3,5,7-trisulphonic acid | 11.4 | 45.5 |
| 2-Nitronaphthalene-3,5,7-trisulphonic acid | 1.7 | 7.0 |

500 ml of the dilute acid nitration mixture solution described above and about 350 ml of 25% strength aqueous ammonia solution are simultaneously allowed to run into 100 ml of water at 0° to 5° C., whilst cooling and stirring and whilst maintaining a pH value of 9. After subsequently stirring the mixture at 20° C. for 2 hours, whilst maintaining a constant pH value, the reaction solution is made up to 1 l with water.

The composition of the reaction solution thus obtained is determined by means of high pressure liquid chromatography, using an acid eluting agent. The solution has the following content of nitronaphthalene-sulphonic acids:

|  | Content (g/l) | Yield, relative to the particular naphthalene-trisulphonic acid (mol %) |
|---|---|---|
| 1-Nitronaphthalene-3,6,8-trisulphonic acid | 77.9 | 96.5 |
| 2-Nitronaphthalene-3,6,8-trisulphonic acid | 0.24 | 0.3 |
| 1-Nitronaphthalene-2,5,7-trisulphonic acid | 2.4 | 3.0 |
| Naphthalene-1,3,6-trisulphonic acid | 0.29 | 0.4 |
| 1-Nitronaphthalene-4,6,8-trisulphonic acid | 6.6 | 79.5 |
| 2-Nitronaphthalene-4,6,8-trisulphonic acid | 0.45 | 5.5 |
| Naphthalene-1,3,5-trisulphonic acid | 0.22 | 3.0 |
| 1-Nitronaphthalene-3,5,7-trisulphonic acid | 5.7 | 46.0 |
| 2-Nitronaphthalene-3,5,7-trisulphonic acid | 0.94 | 7.5 |

EXAMPLE 10

400 g of a naphthalene-trisulphonation mixture which had been obtained as described in Example 1 are initially introduced into the nitration apparatus described in Example 1. The mixture had the following composition: 36.7% of naphthalene-1,3,5-trisulphonic acid, 7.5% of naphthalene-1,3,6-trisulphonic acid, 1.4% of naphthalene-1,3,7-trisulphonic acid and 54% of sulphuric acid. The carbon content of the sulphonation mixture was 15.2%.

40 g of water and 200 g of 90% strength sulphuric acid are first added dropwise to the trisulphonation mixture at 30° C., whilst cooling and stirring, and 99 g (0.75 mol) of ammonium sulphate are also introduced. 48 g (0.75 mol) of 98% strength nitric acid are then added dropwise at 30° C. in the course of 5 minutes, whilst cooling and stirring. The reaction mixture is subsequently stirred at 30° C. for 60 minutes. The nitration mixture is then worked up as described in Example 1, by diluting with water and treating with ammonia. According to high pressure liquid chromatography, the aqueous dilute solution thus obtained has the following content of (nitro)naphthalene-sulphonic acids (to demonstrate the effect of increasing the yield by the addition of a base during working up of the nitration mixture, a portion of the aqueous dilute nitration mixture solution was worked up without the addition of ammonia):

|   | Base | Yield, relative to the particular naphthalene-trisulphonic acid (mol %) |
| --- | --- | --- |
| 1-Nitronaphthalene-3,6,8-trisulphonic acid | none | 63 |
|  | ammonia | 90 |
| 1-Nitronaphthalene-4,6,8-trisulphonic acid | none | 37.5 |
|  | ammonia | 76.5 |
| Naphthalene-1,3,5-trisulphonic acid | none | 4.3 |
|  | ammonia | 4.3 |
| Naphthalene-1,3,6-trisulphonic acid | none | 2.1 |
|  | ammonia | 2.3 |

EXAMPLE 11

The naphthalene-trisulphonation mixture described in Example 1 is nitrated under the conditions described in Example 1. However, the nitration mixture obtained in this manner is then not diluted but introduced, in undiluted form, into 500 g of ice-water at the same time as 25% strength aqueous ammonia solution, whilst cooling and maintaining a pH value of 9.

The composition of the aqueous reaction solution thus obtained is determined by means of high pressure liquid chromatography, using an acid eluting agent. The content of (nitro)naphthalene-sulphonic acids in the solution is:

| — | Base | Yield, relative to the particular naphthalene-trisulphonic acid (mol %) |
| --- | --- | --- |
| 1-Nitronaphthalene-3,6,8-trisulphonic acid | ammonia | 96.5 |
| 1-Nitronaphthalene-4,6,8-trisulphonic acid | ammonia | 76.0 |
| Naphthalene-1,3,5-trisulphonic acid | ammonia | 4.0 |
| Naphthalene-1,3,6-trisulphonic acid | ammonia | 1.5 |

EXAMPLE 12

381 g of a trisulphonation mixture which has been obtained by the process described in F.I.A.T. Final Report No. 1016, pages 42–44 are initially introduced into a nitration apparatus. The trisulphonation mixture had the following composition: 34.7% of naphthalene-1,3,5-trisulphonic acid, 11.0% of naphthalene-1,3,6-trisulphonic acid, 2.15% of naphthalene-1,3,7-trisulphonic acid and sulphuric acid and free $SO_3$ as the remainder. The carbon content was 15.8%.

15 g of water are first added dropwise to this sulphonation mixture at 35° C., whilst cooling, and 33 g (0.25 mol) of ammonium sulphate are also introduced. 48 g (0.75 mol) of 98% strength nitric acid are then added dropwise at 35° C. in the course of 23 minutes, whilst cooling and stirring. The reaction mixture is subsequently stirred at 35° C. for 67 minutes. The nitration mixture is then worked up as described in Example 1, by diluting with water and treating with ammonia.

The yields of nitronaphthalenesulphonic acids are determined by high pressure liquid chromatography, using an acid eluting agent. For comparison, the yields in the acid nitration mixture solution which had not been treated with ammonia are also determined. The yields are given below:

|   | Base | Yield, relative to the particular naphthalene-trisulphonic acid (mol %) |
| --- | --- | --- |
| 1-Nitronaphthalene-3,6,8-trisulphonic acid | none | 81.2 |
|  | ammonia | 94.7 |
| 1-Nitronaphthalene-4,6,8-trisulphonic acid | none | 42.9 |
|  | ammonia | 71.9 |
| Naphthalene-1,3,5-trisulphonic acid | none | 1.4 |
|  | ammonia | 2.4 |
| Naphthalene-1,3,6-trisulphonic acid | none | 0.34 |
|  | ammonia | 0.38 |

EXAMPLE 13

A dilute acid nitration mixture solution which has been prepared according to Example 12 and an aqueous calcium carbonate suspension are simultaneously introduced into a receiver at 70° C., whilst maintaining a pH value of 2. The reaction mixture thus obtained is subsequently stirred at 70° C. for 30 minutes. The pH value is kept at 2, if necessary by adding a little sulphuric acid. After filtering off the gypsum which has precipitated and washing it with warm water, the combined filtrates and 25% strength aqueous ammonia solution are allowed to run simultaneously into a receiver at 20° C., whilst maintaining a pH value of 9. After stirring the mixture for 2 hours, whilst maintaining the pH value, the yield of nitronaphthalene-sulphonic acids in the aqueous reaction solution is determined by high pressure liquid chromatography, using an acid eluting agent. The yields of nitronaphthalene-sulphonic acids and—for comparison—the yields in the reaction solution which has only been adjusted to a pH value of 2 with calcium carbonate are summarised below.

| Base | Yield, relative to the particular naphthalene-trisulphonic acid (mol %) |
|---|---|---|
| 1-Nitronaphthalene-3,6,8-trisulphonic acid | none | 82.5 |
| | ammonia | 95.1 |
| 1-Nitronaphthalene-4,6,8-trisulphonic acid | none | 44.4 |
| | ammonia | 68.9 |
| Naphthalene-1,3,5-trisulphonic acid | none | 1.96 |
| | ammonia | 3.60 |
| Naphthalene-1,3,6-trisulphonic acid | none | 0.28 |
| | ammonia | 0.30 |

EXAMPLE 14

150 ml of 98% strength nitric acid are initially introduced into a nitration apparatus. 107 g (0.15 mol) of naphthalene-1,3,5-trisulphonic acid (composition: 51.6% of naphthalene-1,3,5-trisulphonic acid, 29.5% of sulphuric acid and 19% of water) are introduced into this apparatus at −20° to −15° C. in the course of 40 minutes, whilst cooling with dry ice/acetone. The reaction mixture is subsequently stirred at −20° to −15° C. for 90 minutes and is then poured, at 0° to 5° C., onto about 1000 g of ice, whilst cooling. The yields of nitronaphthalene-sulphonic acids in the aqueous reaction solution thus obtained are determined by high pressure liquid chromatography, using an acid eluting agent.

The dilute aqueous nitration mixture solution described above is adjusted to a pH value of 9.5 to 10 at 0° to 5° C. by adding 25% strength aqueous ammonia solution and is stirred at this pH value for 5 hours. The yield of nitronaphthalene-sulphonic acid in the reaction solution thus obtained is then determined by high pressure liquid chromatography, using an acid eluting agent. The yields of nitronaphthalene-sulphonic acid in the acid nitration mixture solution and in the reaction solution which has been treated with ammonia are summarised below.

| | Base | Yield (mol %) |
|---|---|---|
| 1-Nitronaphthalene-4,6,8-trisulphonic acid | none | 39.6 |
| | ammonia | 86 |
| 2-Nitronaphthalene-4,6,8-trisulphonic acid | none | 8.5 |
| | ammonia | 10.5 |
| Naphthalene-1,3,5-trisulphonic acid | none | 0.1 |
| | ammonia | 0.7 |

EXAMPLE 15

Naphthalene-1,3,5-trisulphonic acid is nitrated as described in Example 14. However, before diluting the nitration mixture with ice, the excess nitric acid is distilled off under a high vacuum at −20° to −10° C. in the course of 4 hours. As in Example 14, the yields of nitronaphthalenesulphonic acids, both in the acid nitration mixture solution and in the aqueous reaction solution obtained after the treatment with ammonia, are determined by high pressure liquid chromatography, using an acid eluting agent. The yields are summarised below.

| | Base | Yield (mol %) |
|---|---|---|
| 1-Nitronaphthalene-4,6,8-trisulphonic acid | none | 41 |
| | ammonia | 85 |
| 2-Nitronaphthalene-4,6,8-trisulphonic acid | none | 7 |
| | ammonia | 11 |
| Naphthalene-1,3,5-trisulphonic acid | none | 0.2 |
| | ammonia | 1.5 |

EXAMPLE 16

(Comparison example; nitration according to F.I.A.T. Final Report, No. 1016, pages 42–44)

381 g of a naphthalene-trisulphonation mixture which has been prepared according to F.I.A.T. Final Report No. 1016, pages 42–44 are initially introduced into a nitration apparatus.

The mixture had the following composition: 33.1% of naphthalene-1,3,5-trisulphonic acid, 10.8% of naphthalene-1,3,6-trisulphonic acid, 2.2% of naphthalene-1,3,7-trisulphonic acid and sulphuric acid and excess $SO_3$ as the remainder. The carbon content was 15.0%.

The sulphonation mixture is diluted with 25 g of water at 60° C. and nitrated with 43 g (=0.587 mol of nitric acid) of mixed acid (composition: 86% of nitric acid, 12% of sulphuric acid and 2% of water) at 30° to 35° C. in the course of 12 hours, and the nitration mixture is subsequently stirred at 40° C. for 1 hour.

A sample of this nitration mixture is poured onto ice and the yield of nitronaphthalene-sulphonic acids in this dilute acid nitration mixture solution is determined by means of high pressure liquid chromatography, using an acid eluting agent.

A portion of this dilute acid nitration mixture solution is adjusted to a pH value of 9 with 25% strength aqueous ammonia solution. The yield of (nitro)naphthalene-sulphonic acids in this solution is likewise determined by means of high pressure liquid chromatography, using an acid eluting agent.

Most of the nitration mixture is poured into water, in accordance with F.I.A.T. Final Report No. 1016, pages 42–44. The solution formed is freed from nitrous gases and then neutralised with calcium carbonate. After filtering off the gypsum, the yield of naphthalenesulphonic acids in the aqueous solution is determined by means of high pressure liquid chromatography, using an acid eluting agent.

The yields of nitro-naphthalene-sulphonic acids in the various solutions are summarised in Table 5.

TABLE 5

| | | | Yield [mol %] | |
|---|---|---|---|---|
| | Base | pH value | Relative to the particular naphthalene-sulphonic acid | Relative to the naphthalene employed |
| 1-Nitronaphthalene-3,6,8-trisulphonic acid | none | <1 | 94.5 | 21.1 |
| | ammonia | 9 | 94.8 | 21.2 |
| | CaCO$_3$ | | 93.6 | 21.0 |
| 1-Nitronaphthalene-4,6,8-trisulphonic acid | none | <1 | 45.2 | 30.9 |
| | ammonia | 9 | 48.1 | 32.9 |

TABLE 5-continued

|  | Base | pH value | Yield [mol %] Relative to the particular naphthalene-sulphonic acid | Relative to the naphthalene employed |
|---|---|---|---|---|
|  | CaCO$_3$ |  | 45.6 | 31.2 |
| Naphthalene-1,3,5-trisulphonic acid | none | <1 | 14.8 | 10.2 |
|  | ammonia |  | 15.1 | 10.3 |
|  | CaCO$_3$ |  | 18.7 | 12.8 |
| Naphthalene-1,3,6-trisulphonic acid | none | <1 | 0.6 | 0.13 |
|  | ammonia | 9 | 0.5 | 0.11 |
|  | CaCO$_3$ |  | 0.5 | 0.11 |

EXAMPLE 17

903 g of a nitration mixture which has been obtained by nitrating 0.5 mol of pure naphthalene-1,5-disulphonic acid according to the process described in U.S. Pat. No. 2,191,820 are initially introduced into a nitration apparatus. The nitration mixture is diluted with 65 g of water at 20° C. and cooled to 10° C., and 64.3 g (1.0 mol) of 98% strength nitric acid are added at 10° C. in the course of 10 minutes, whilst stirring and cooling. The reaction mixture is subsequently stirred at 10° C. for 170 minutes and then poured onto 300 g of ice, during which a temperature of 10° C. is not exceeded.

The composition of the dilute acid nitration mixture solution obtained in this manner is determined by means of high pressure liquid chromatography, using an acid eluting agent. The dilute acidnitration mixture solution and 25% strength aqueous ammonia solution are simultaneously introduced into a receiver at 20° to 25° C., whilst maintaining a pH value of 9, and the pH value is kept constant at 9 for four hours.

The reaction mixture is then adjusted to a pH value of 4 with sulphuric acid. After leaving the mixture to stand for several hours, the product which has precipitated is filtered off, washed with saturated ammonium sulphate solution and dried at 50° C. in vacuo. Yield: 187 g of dry product. This product contains 55.5% of 3,8-dinitronaphthalene-1,5-disulphonic acid, that is to say 54.9%, relative to the naphthalene-1,5-disulphonic acid employed.

The yields of 3,8-dinitronaphthalene-1,5-disulphonic acid in the dilute acid nitration mixture solution and in the dilute solution which has been treated with ammonia are given below:

|  | Base | Yield, relative to the naphthalene-1,5-disulphonic acid (mol %) |
|---|---|---|
| 3,8-Dinitronaphthalene-1,5-disulphonic acid | none | 33.8 |
|  | ammonia | 60.9 |

EXAMPLE 18

The nitration reaction described in Example 17 is repeated, with the modification that the nitration mixture obtained according to U.S. Pat. No. 2,191,820 was nitrated in the presence of 66.1 g (0.5 mol) of ammonium sulphate at temperatures of 30° C. in the course of 10 minutes and the nitration mixture is subsequently stirred at 30° C. for 80 minutes.

173.2 g of dry product with a content of 3,8-dinitronaphthalene-1,5-disulphonic acid of 66% (60.48%, relative to the naphthalene-1,5-disulphonic acid) are obtained.

The yields of 3,8-dinitronaphthalene-1,5-disulphonic acid in the dilute acid nitration mixture solution and in the dilute aqueous reaction solution which has been treated with ammonia are given below.

|  | Base | Yield, relative to the naphthalene-1,5-disulphonic acid (mol %) |
|---|---|---|
| 3,8-Dinitronaphthalene-1,5-disulphonic acid | none | 33.52 |
|  | ammonia | 64.83 |

EXAMPLE 19

(Comparison example; nitration according to German Patent Specification 72,665)

3-Nitronaphthalene-1,5-disulphonic acid is nitrated with nitric acid in sulphuric acid at 90° C. as described in German Patent Specification 72,665. After a reaction time of 85 hours, the yield of 3,8-dinitronaphthalene-1,5-disulphonic acid is 48%, relative to the 3-nitronaphthalene-1,5-disulphonic acid employed.

For comparison, the acid nitration mixture solution which has been diluted with water is adjusted to a pH value of 9 with 25% strength aqueous ammonia solution and was kept at this pH value for 4 hours. The yield of 3,8-dinitronaphthalene-1,5-disulphonic acid is unchanged at 48% of theory.

EXAMPLE 20

16,2 g (0,05 mol) of naphthalene-1,5-disulphonic acid (diammonium salt) are introduced with stirring at −10° to −20° C. onto 289 g of 90% strength sulphuric acid. 3,86 g of 98% strength nitric acid are then added to this mixture within 6 minutes. After stirring for further 6 minutes the reaction mixture is poured onto 435 g of ice.

A sample (Sample 1) is taken from the aqueous acidic solution thus obtained. The remaining solution is adjusted to a $p_H$-value of 9 by the addition of 444 ml 25% strength aqueous ammonia solution with stirring and cooling at a temperature between 0° and 25° C., is stored for two hours at 20° C. and is then adjusted to a $p_H$-value of 3 by the addition of 17 ml 50% strength sulphuric acid. A sample (Sample 2) is also taken from this solution.

The content of both Samples 1 and 2 is determined by high pressure liquid chromatography, using an acidic elution agent. There are obtained the following yields (in mol-%) relative to the naphthalene-1,5-disulphonic acid diammonium salt initially used:

| in | | |
|---|---|---|
| Sample 1 | Sample 2 | |
| 8,56 | 8,34 | naphthalene-1,5-disulphonic acid |
| 43,29 | 66,16 | 1-nitronaphthalene-4,8-disulphonic acid |
| 26,76 | 27,26 | 2-nitronaphthalene-4,8-disulphonic acid |

What is claimed is:

1. In the process for the preparation of α-nitronaphthalene-sulphonic acids of the formula

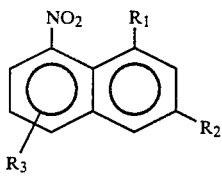

in which
R$_3$ is in the 5-position or 6-position,
R$_1$ and R$_3$ independently of one another are a SO$_3$H group or NO$_2$ group and
R$_2$ is a hydrogen atom or a SO$_3$H group or NO$_2$ group, with the proviso that at least one of the substituents R$_1$, R$_2$ or R$_3$ is a SO$_3$H group,
by reacting the corresponding naphthalene-sulphonic acids of the formula

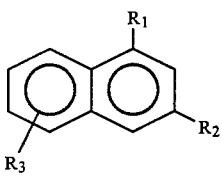

in which R$_1$, R$_2$ and R$_3$ have the above stated meaning with nitric acid and working up the nitration mixture, the improvement comprising
(a) interrupting the reaction of the naphthalene-sulphonic acids with nitric acid already before the nitration reaction has ended and
(b) treating the nitration mixture, if appropriate after dilution with water, with bases at a pH value of 5 to 14.

2. The process according to claim 1, wherein in the reaction of naphthalene-1,3,6-trisulphonic acid with nitric acid, the nitration reaction is interrupted as soon as more than 90% of the naphthalene-1,3,6-trisulphonic acid employed has reacted, and the yield of 8-nitronaphthalene-1,3,6-trisulphonic acid in the nitration mixture is at most 90% of the theoretical yield, relative to naphthalene-1,3,6-trisulphonic acid.

3. The process according to claim 1 wherein in the reaction of naphthalene-1,3,5-trisulphonic acid with nitric acid, the nitration reaction is interrupted as soon as more than 90% of the naphthalene-1,3,5-trisulphonic acid employed has reacted, and the yield of 8-nitronaphthalene-1,3,5-trisulphonic acid in the nitration mixture is at most 50% of the theoretical yield, relative to naphthalene-1,3,5-trisulphonic acid.

4. The process according to claim 1 wherein in the reaction of 3-nitronaphthalene-1,5-disulphonic acid with nitric acid, the nitration reaction is interrupted as soon as more than 90% of the 3-nitronaphthalene-1,5-disulphonic acid employed has reacted, and the yield of 3,8-dinitronaphthalene-1,5-disulphonic acid in the nitration mixture is at most 50% of the theoretical yield, relative to 3-nitronaphthalene-1,5-disulphonic acid.

5. The process according to claim 1 wherein the reaction of the naphthalenesulphonic acid with nitric acid is carried out in 85 to 95% strength by weight sulphuric acid at temperatures from 0° to 50° C., and 1.05 to 2.5 mols of nitric acid are employed per mol of naphthalenesulphonic acid.

6. The process according to claim 1 wherein the reaction of the naphthalenesulphonic acid with nitric acid is carried out in excess 80 to 100% strength by weight nitric acid at temperatures from −40° to +20° C.

7. The process according to claim 1 wherein the reaction of the naphthalenesulphonic acids with nitric acid is carried out in the presence of alkali metal sulphates.

8. The process according to claim 1 wherein the nitration mixture obtained in the reaction of naphthalene-1,3,6-trisulphonic acid with nitric acid, which mixture has been diluted with water if necessary, is treated with inorganic and/or organic bases at a pH value of 5 to 10 and at temperatures of −10° to +130° C., until the content of 8-nitronaphthalene-1,3,6-trisulphonic acid in the treated nitration mixture no longer increases.

9. The process according to claim 1 wherein the nitration mixture which is obtained in the reaction of naphthalene-1,3,5-trisulphonic acid or 3-nitronaphthalene-1,5-disulphonic acid with nitric acid and which has been diluted with water if necessary is treated with ammonia and/or organic bases at a pH value of 5 to 10 and at temperatures of −10° to +80° C., until the content of 8-nitronaphthalene-1,3,5-trisulphonic acid or 3,8-dinitronaphthalene-1,5-disulphonic acid in the treated nitration mixture no longer increases.

* * * * *